(12) United States Patent
Hong et al.

(10) Patent No.: US 8,039,048 B2
(45) Date of Patent: Oct. 18, 2011

(54) ALGAE RESISTANT ROOFING GRANULES WITH CONTROLLED ALGAECIDE LEACHING RATES, ALGAE RESISTANT SHINGLES AND PROCESS FOR PRODUCING SAME

(75) Inventors: Keith C. Hong, Northborough, MA (US); Husnu M. Kalkanoglu, Swarthmore, PA (US); Ming Liang Shiao, Collegeville, PA (US)

(73) Assignee: CertainTeed Corporation, Valley Forge, PA (US)

( * ) Notice: Subject to any disclaimer, the term of this patent is extended or adjusted under 35 U.S.C. 154(b) by 80 days.

(21) Appl. No.: 12/610,782

(22) Filed: Nov. 2, 2009

(65) Prior Publication Data

US 2010/0047524 A1 Feb. 25, 2010

Related U.S. Application Data

(62) Division of application No. 10/600,847, filed on Jun. 20, 2003, now Pat. No. 7,687,106.

(51) Int. Cl.
*B05D 7/00* (2006.01)
*B05D 1/24* (2006.01)
(52) U.S. Cl. ......... 427/186; 427/212; 427/214; 427/219
(58) Field of Classification Search .................. 427/186, 427/212, 214, 219
See application file for complete search history.

(56) References Cited

U.S. PATENT DOCUMENTS

| 1,677,701 | A | 7/1928 | Alton |
|---|---|---|---|
| RE19,372 | E | 11/1934 | Walton |
| 2,001,448 | A | 5/1935 | Beasley |
| RE20,295 | E | 3/1937 | Fisher |
| 2,142,540 | A | 1/1939 | Veazey |
| 2,147,058 | A | 2/1939 | Randall et al. |
| 2,379,358 | A | 6/1945 | Jewett |
| 2,591,149 | A | 4/1952 | Grove |
| 2,614,051 | A | 10/1952 | Buzzell et al. |
| 2,695,851 | A | 11/1954 | Lodge |
| 2,799,241 | A | 7/1957 | Wurster et al. |
| 2,898,232 | A | 8/1959 | Miller et al. |
| 2,978,340 | A | 4/1961 | Veatch at al. |
| 2,981,636 | A | 4/1961 | Lodge et al. |
| 2,986,476 | A | 5/1961 | Larssen |
| 3,030,215 | A | 4/1962 | Veatch et al. |
| 3,089,824 | A | 5/1963 | Wurster |
| 3,117,027 | A | 1/1964 | Lindlof et al. |

(Continued)

FOREIGN PATENT DOCUMENTS

JP 2002018358 A 1/2000

OTHER PUBLICATIONS

"The Aging Process of Shingles" by Tyler Wierman, 4 pgs., date unknown.

(Continued)

*Primary Examiner* — Elena T Lightfoot
(74) *Attorney, Agent, or Firm* — Paul & Paul

(57) ABSTRACT

A process for forming algae-resistant roofing shingles comprises producing algae-resistant granules, and adhering the granules to a shingle stock material. The algae-resistant roofing granules are produced by a process that includes coating mineral particles with a clay-silicate binder including a metal oxide algaecide and small organic particles. The particles are heated to cure the binder, and the organic particles pyrolyse to form pores in the coating. The release of the algaecide is controlled by the structure of the granules.

19 Claims, 3 Drawing Sheets

U.S. PATENT DOCUMENTS

| | | |
|---|---|---|
| 3,129,086 A | 4/1964 | Veatch et al. |
| 3,196,827 A | 7/1965 | Wurster et al. |
| 3,207,824 A | 9/1965 | Wurster et al. |
| 3,230,064 A | 1/1966 | Veatch et al. |
| 3,241,520 A | 3/1966 | Wurster et al. |
| 3,253,944 A | 5/1966 | Wurster |
| 3,255,031 A | 6/1966 | Lodge et al. |
| 3,365,315 A | 1/1968 | Beck et al. |
| 3,397,073 A | 8/1968 | Fehner |
| 3,479,201 A | 11/1969 | Sloan |
| 3,507,676 A | 4/1970 | McMahon |
| 3,528,842 A | 9/1970 | Skadulis |
| 3,752,696 A | 8/1973 | Beyard et al. |
| 3,792,136 A | 2/1974 | Schmitt |
| 3,918,407 A | 11/1975 | Greenberg |
| 3,932,143 A | 1/1976 | Marshall et al. |
| 3,945,945 A | 3/1976 | Kiovsky et al. |
| 3,961,628 A | 6/1976 | Arnold |
| 3,985,540 A | 10/1976 | Fein et al. |
| 4,092,441 A | 5/1978 | Meyer et al. |
| 4,111,713 A | 9/1978 | Beck |
| 4,279,632 A | 7/1981 | Frosch et al. |
| 4,378,408 A | 3/1983 | Joedicke |
| 4,391,646 A | 7/1983 | Howell |
| 4,623,588 A | 11/1986 | Nuwayser et al. |
| 4,631,267 A | 12/1986 | Lachman et al. |
| 4,675,140 A | 6/1987 | Sparks et al. |
| 4,735,975 A | 4/1988 | Iwata et al. |
| 4,744,831 A | 5/1988 | Beck |
| 4,767,726 A | 8/1988 | Marshall |
| 4,920,090 A | 4/1990 | Ritter et al. |
| 4,946,505 A | 8/1990 | Jungk |
| 5,022,897 A | 6/1991 | Balcar et al. |
| 5,039,311 A | 8/1991 | Bloecher |
| 5,052,162 A | 10/1991 | Bush et al. |
| 5,077,241 A | 12/1991 | Moh et al. |
| 5,147,686 A | 9/1992 | Ichimura et al. |
| 5,180,585 A | 1/1993 | Jacobson et al. |
| 5,225,123 A | 7/1993 | Torbin |
| 5,240,760 A | 8/1993 | George et al. |
| 5,356,664 A | 10/1994 | Narayan et al. |
| 5,362,566 A | 11/1994 | George et al. |
| 5,366,767 A | 11/1994 | Howard |
| 5,397,759 A | 3/1995 | Torbin |
| 5,411,803 A | 5/1995 | George et al. |
| 5,456,785 A | 10/1995 | Venable |
| 5,503,840 A | 4/1996 | Jacobson et al. |
| 5,595,750 A | 1/1997 | Jacobson et al. |
| 5,599,586 A | 2/1997 | Israel |
| 5,620,554 A | 4/1997 | Venable |
| 5,643,399 A | 7/1997 | Venable |
| 5,713,974 A | 2/1998 | Martin et al. |
| 5,723,516 A | 3/1998 | Bigham et al. |
| 5,733,842 A | 3/1998 | Gerdes et al. |
| 5,888,930 A | 3/1999 | Smith et al. |
| 5,975,988 A | 11/1999 | Christianson |
| 6,063,849 A | 5/2000 | Morris et al. |
| 6,120,913 A | 9/2000 | Kluttz et al. |
| 6,143,318 A | 11/2000 | Gilchrist et al. |
| 6,156,245 A | 12/2000 | Takebayashi et al. |
| 6,214,466 B1 | 4/2001 | Joedicke |
| 6,235,372 B1 | 5/2001 | Joedicke |
| 6,238,794 B1 | 5/2001 | Beesley et al. |
| 6,245,381 B1 | 6/2001 | Israel |
| 6,245,850 B1 | 6/2001 | Fields |
| 6,296,912 B1 | 10/2001 | Zickell |
| 6,306,795 B1 | 10/2001 | Ryan et al. |
| 6,495,074 B1 | 12/2002 | Carr |
| 6,502,360 B2 | 1/2003 | Carr, III et al. |
| 6,531,200 B2 | 3/2003 | Zickell et al. |
| 6,797,277 B2 | 9/2004 | Heier et al. |
| 6,861,145 B2 | 3/2005 | Nastke et al. |
| 6,936,644 B2 | 8/2005 | Gilleo |
| 2002/0095871 A1 | 7/2002 | McArdle et al. |
| 2002/0098110 A1 | 7/2002 | Graham et al. |
| 2002/0160151 A1 | 10/2002 | Pinault et al. |
| 2003/0037698 A1 | 2/2003 | Kiik et al. |
| 2003/0068303 A1 | 4/2003 | Selvig et al. |
| 2003/0068469 A1 | 4/2003 | Aschenbeck et al. |
| 2003/0108668 A1 | 6/2003 | Joedicke |
| 2004/0110639 A1 | 6/2004 | Joedicke |
| 2005/0053745 A1 | 3/2005 | Bartek et al. |
| 2005/0053746 A1 | 3/2005 | Bartek |
| 2005/0064175 A1 | 3/2005 | Azari et al. |
| 2005/0072114 A1 | 4/2005 | Shiao et al. |
| 2005/0074580 A1 | 4/2005 | Gross et al. |
| 2008/0095984 A1 | 4/2008 | Desouto |
| 2008/0131664 A1 | 6/2008 | Teng et al. |
| 2009/0047474 A1 | 2/2009 | Gross et al. |
| 2009/0117329 A1 | 5/2009 | Leitch et al. |

OTHER PUBLICATIONS

Technical Bulletin Asphalt Roofing Manufactures Association "Algae Discoloration of Roofs," Catalogue No. 217-RR-89, 1 pg., (Calverton, MD), May 1997.

Copper Development Association Inc., "Copper Blocks ugly Bugs," 2 pgs., Winter 1995.

Johns Manville Roofing Systems Group, "Roofing Granules" Sheet ID: 3004, 6 pgs. (Denver, CO) Issued Jan. 11, 2001.

Minerals Research & Recovery, Inc. "Roofing Granules," 2 pgs. (Tuscan, AZ) date unknown.

"Location Affects Performance of Biocide-Containing Paints" by I. Colon, Ph.D.; E.L. Kuusisto; and K. Hansen/Troy Corporation, Florham Park, NJ, Nov. 2004.

"Biocide Optimization: Blends of Actives" by Karen Winkowski, Ph.D. International Speciality Products, Wayne, NJ, Jul. 2004.

"Algae on the Roof: A Growing Problem" by Shawn Holiday, Jun. 2005.

ALGAE RESISTANT ROOFING GRANULES WITH CONTROLLED ALGAECIDE LEACHING RATES, ALGAE RESISTANT SHINGLES AND PROCESS FOR PRODUCING SAME

CROSS REFERENCE TO RELATED APPLICATION

This application is a division of pending U.S. patent application Ser. No. 10/600,847, filed Jun. 20, 2003.

BACKGROUND OF THE INVENTION

1. Field of the Invention

The present invention relates to asphalt roofing shingles, and protective granules for such shingles, and processes for makings such granules and shingles.

2. Brief Description of the Prior Art

Pigment-coated mineral rocks are commonly used as color granules in roofing applications to provide aesthetic as well as protective functions to the asphalt shingles. Dark blotches or streaks sometimes appear on the surfaces of asphalt shingles, especially in warmer humid climates, as a result of the growth of algae and other microorganisms. The predominant species responsible is *Gloeocapsa magma*, a blue green algae. Eventually, severe discoloration of the entire roof can occur.

Various methods have been used in an attempt to remedy the roofing discoloration. For example, topical treatments with organic algaecides have been used. However, such topical treatments are usually effective only for short term, typically one to two years. Another approach is to add algaecidal metal oxides to the color granule coatings. This approach is likely to provide longer protection, for example, as long as ten years.

Companies, including Minnesota Mining and Manufacturing (3M) and GAF Materials Corporation/ISP Mineral Products Inc., have commercialized several algaecide granules that are effective in inhibiting algae growth.

A common method used to prepare algae-resistant (AR) roofing granules generally involves two major steps. In the first step, metal oxides such as cuprous oxide and zinc oxide are added to a clay and alkali metal silicate mixture that in turn is used to coat crushed mineral rocks. The mixture is rendered insoluble on the rock surfaces by firing at high temperatures, such as about 500° C., to provide a ceramic coating. In the second step, the oxides covered rocks are coated with various color pigments to form colored algae-resistant roofing granules. The algae-resistant granules, alone, or in a mixture with conventional granules, are then used in the manufacture of asphalt shingles using conventional techniques. The presence of the algae-resistant granules confers algae-resistance on the shingles.

Roofing granules typically comprise crushed and screened mineral materials, which are subsequently coated with a binder containing one or more coloring pigments, such as suitable metal oxides. The binder can be a soluble alkaline silicate that is subsequently insolubilized by heat or by chemical reaction, such as by reaction between an acidic material and the alkaline silicate, resulting in an insoluble colored coating on the mineral particles.

U.S. Pat. No. 3,507,676 discloses roofing granules containing zinc, zinc oxide, or zinc sulfide, as an algaecide and fungicide.

Algae-resistant shingles are disclosed, for example, in U.S. Pat. No. 5,356,664 assigned to Minnesota Mining and Manufacturing Co., which discloses the use of a blend of algae-resistant granules and non-algae-resistant granules. The algae-resistant granules have an inner ceramic coating comprising cuprous oxide and an outer seal coating initially devoid of copper.

There is a continuing need for algae-resistant roofing products having algaecide leaching rates that can be controlled so that the roofing products can be tailored for specific local conditions.

SUMMARY OF THE INVENTION

The present invention provides algae-resistant roofing granules having algaecide leaching rates that can be easily controlled, and asphalt shingle roofing products incorporating such algae-resistant roofing granules.

The present invention employs mineral particles to form algae-resistant roofing granules. In contrast to prior processes for forming algae-resistant granules, which typically rely only upon porosity developed during cure of a ceramic binder, typically a sodium silicate/aluminosilicate binder cured chemically or thermally, the process of the present invention employs void-forming additives to contribute to porosity and thus control the leach rate of algaecidal material from the roofing granules.

This invention thus provides a process for preparing algae-resistant roofing granules having algaecide leaching rates that can be controlled and modified at will.

The present process for producing algae-resistant roofing granules comprises providing inert base particles and forming first intermediate particles by coating the inert base particles with a first mixture to form a first layer on the inert base particles. The inert particles can be, for example, crushed rock. The first mixture includes at least one algaecidal material, a void-forming material, and preferably, a binder. The binder can include an aluminosilicate material such as clay, and a soluble silicate, such as aqueous sodium silicate. The void-forming material preferably releases gaseous material above 90° C., and has an average particle size no larger than about 2 mm. The void-forming material can be decomposable into gaseous by-products at temperatures above about 150° C. In the alternative, the void forming material can simply release moisture as a gaseous material to form the desired voids.

The present process preferably further comprises forming second intermediate particles by coating the first intermediate particles with a second mixture including a coloring material. The second mixture can include a binder, such as a binder having the same composition as the first mixture. The second mixture can also optionally comprise a void-forming material. Further, the second mixture can optionally include at least one algaecidal material.

The process requires heating the first and/or second intermediate particles, preferably above the temperature at which the gaseous material is released, to release the gaseous material and form pores in the first layer to produce the roofing granules.

Metal oxides are preferred as algaecidal materials due to their favorable cost and performance. The at least one algaecidal material is preferably selected from the group consisting of copper compounds and zinc compounds. For example, cuprous oxide and/or zinc oxide can be employed. In one presently preferred embodiment of the present invention, both cuprous oxide and zinc oxide are used, and the cuprous oxide comprises about 2 to 6 percent of the algae-resistant granules, and the zinc oxide comprises about 0.1 to 2 percent by weight of the algae-resistant granules.

The void-forming material can be an organic or inorganic compound, and can be either water soluble or insoluble. Examples of decomposable void-forming materials include sugar, crushed nuts (such as walnut shells), crushed corn and grains, carbon or graphite balls, synthetic and natural polymers, organic fibers, flame retardants and hydrated compounds.

The void-forming material preferably comprises a substance selected from the group consisting of ground walnut shells, sugar, and carbon black. In one presently preferred embodiment of the present invention, the void-forming material comprises about 0.5 to 5 percent by weight of the algae-resistant granules.

The void-forming material can release gaseous material, or decompose or evaporate at elevated temperature, leaving behind hollow openings that provide additional avenues for the metal ions to leach out easily.

The present invention also provides a process for producing algae-resistant roofing shingles, as well as the shingles themselves. This process comprises producing algae-resistant roofing granules using the process of this invention, and adhering the granules to a shingle stock material.

The algaecidal material concentration preferably is from about 0.1% to about 10% of the total granule weight, and that of the void-forming material is preferably from about 0.05 to about 5%. Various combinations of the levels and types of the void-forming materials used in the formulations can provide different amounts of algaecidal material leaching out from the granules.

The algae-resistant granules prepared according to the process of the present invention can be employed in the manufacture of algae-resistant roofing products, such as algae-resistant asphalt shingles. The algae-resistant granules of the present invention can be mixed with conventional roofing granules, and the granule mixture can be embedded in the surface of bituminous roofing products using conventional methods. Alternatively, the algae-resistant granules of the present invention can be substituted for conventional roofing granules in manufacture of bituminous roofing products, such as asphalt roofing shingles, to provide those roofing products with algae-resistance.

In one embodiment, the present invention provides a process for preparing AR roofing granules having a controllable algaecide-leaching rate.

In another embodiment, the present invention provides a process for preparing roofing shingles having algae-resistance that can be customized to the specific geographic region in which the shingles are intended to be used.

The present invention preferably provides algae-resistant roofing granules having controllable levels of algaecide release.

The present invention also preferably provides algae resistant asphalt shingles.

DETAILED DESCRIPTION OF THE PREFERRED EMBODIMENT

Figure 1:
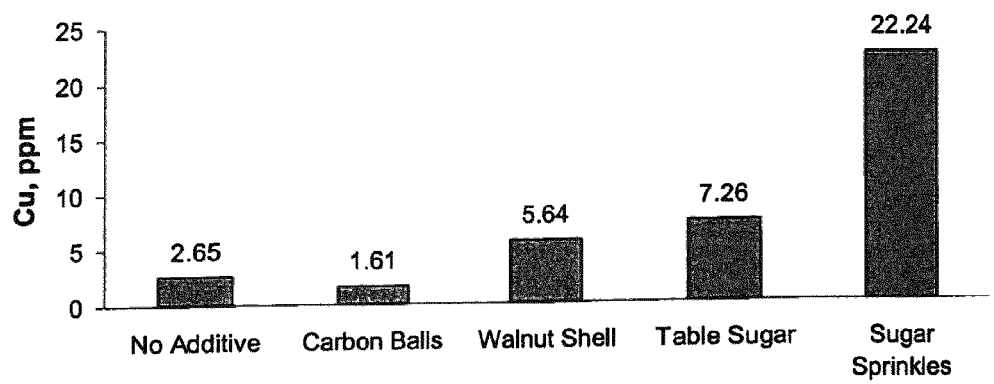
FIG. 1 is a graph illustrating the effect of various types of void-forming material on the concentrations of copper ions leached out from granules prepared according to the present invention (after 8 days immersion in warm water of 60° C.). The values above the bars depict the copper concentrations in ppm.

The inert base particles employed in the process of the present invention are preferably chemically inert materials, such as inert mineral particles. The mineral particles, which can be produced by a series of quarrying, crushing, and screening operations, are generally intermediate between sand and gravel in size (that is, between about 8 US mesh and 40 US mesh), and preferably have an average particle size of from about 0.2 mm to about 3 mm, and more preferable from about 0.4 mm to about 2.4 mm.

In particular, suitably sized particles of naturally occurring materials such as talc, slag, granite, silica sand, greenstone, andesite, porphyry, marble, syenite, rhyolite, diabase, greystone, quartz, slate, trap rock, basalt, and marine shells can be used, as well as recycled manufactured materials such as crushed bricks, concrete, porcelain, fire clay, and the like.

The process of the present invention for producing algae-resistant roofing granules comprises providing inert base particles, and forming first intermediate particles by coating the inert base particles with a first mixture to form a first layer on the inert base particles. This first mixture includes at least one algaecidal material, at least one void-forming material, and, preferably, a binder.

The void-forming material can be an organic material or inorganic compound. Preferably, the void-forming material is selected so that it releases gaseous material, such as by decomposing into gaseous products, at suitably elevated temperatures. The void-forming material preferably releases gaseous material at a temperature that is greater than 90 degrees C. The void-forming material may, for example, release bound water, or water of hydration, at the elevated temperature. In the alternative, the void-forming material may itself decompose at an elevated temperature, preferably at a temperature above about 150 degrees C. Examples of void-forming materials include sugar, sugar-based products such as candy "sprinkles," crushed nuts (such as walnut shells), crushed corn and grains, carbon or graphite balls, synthetic and natural polymers, organic fibers, flame-retardants, and hydrated compounds. The void-forming material can be either water-soluble or water-insoluble. Preferably, the void-forming material comprises at least 0.1 percent by weight of the algae-resistant granules. Preferably, the void-forming material has an average particle size no larger than about 2 mm. The void-forming material preferably has an average particle size from about 100 μm to about 400 μm. Mixtures of void-forming materials can also be used, as well as mixture of water-soluble and water-insoluble void-forming material. The proportions of mixtures of void-forming materials can be tailored to achieve desired leaching characteristics for the resulting algae-resistant particles. The void-forming material preferably comprises a substance selected from the group consisting of ground walnut shells, sugar, and carbon black. In one presently preferred embodiment of the present invention, the void-forming material comprises about 1.4 percent by weight of the algae-resistant granules.

The at least one algaecide is preferably selected from the group consisting of copper materials, zinc materials, and mixtures thereof. For example, cuprous oxide and/or zinc oxide, or a mixture thereof, can be used. The copper materials that can be used in the process of the present invention include cuprous oxide, cupric acetate, cupric chloride, cupric nitrate, cupric oxide, cupric sulfate, cupric sulfide, cupric stearate, cupric cyanide, cuprous cyanide, cuprous stannate, cuprous thiocyanate, cupric silicate, cuprous chloride, cupric iodide, cupric bromide, cupric carbonate, cupric fluoroborate, and mixtures thereof. The zinc materials can include zinc oxide, such as French process zinc oxide, zinc sulfide, zinc borate, zinc sulfate, zinc pyrithione, zinc ricinoleate, zinc stearate, zinc chromate, and mixtures thereof. In one embodiment, the at least one algaecide preferably comprises cuprous oxide, and it is preferred that the cuprous oxide comprises at least 2 percent of the algae resistant granules. In another embodiment, the at least one algaecide preferably comprises zinc oxide, and it is preferred that the zinc oxide comprises at least 0.1 percent by weight of the algae-resistant granules. When a mixed algaecide is employed, the at least one algaecide preferably comprises a mixture of cuprous oxide and zinc oxide.

The binder employed in the process of the present invention to form the first intermediate particles is preferably formed from a mixture of an alkali metal silicate, such as aqueous sodium silicate, and heat reactive aluminosilicate material, such as clay, preferably, kaolin. The proportion of alkali metal silicate to heat-reactive aluminosilicate material is preferably from about 3:1 to about 1:3 parts by weight alkali metal silicate to parts by weight heat-reactive aluminosilicate material, more preferably about 2:1 to about 0.8:1 parts by weight alkali metal silicate to parts by weight heat-reactive aluminosilicate material.

When the algae-resistant granules are fired at an elevated temperature, such as at least about 200 degrees C., and preferably about 250 to 500 degrees C., the clay reacts with and neutralizes the alkali metal silicate, thereby insolubilizing the binder. The binder resulting from this clay-silicate process, believed to be a sodium aluminum silicate, is porous, such as disclosed in U.S. Pat. No. 2,379,358 (incorporated herein by reference). Alternatively, the porosity of the insolubilized binder can be decreased by including an oxygen containing boron compound such as borax in the binder mixture, and firing the granules at a lower temperature, for example, about 250 degree C. to 400 degrees C., such as disclosed in U.S. Pat. No. 3,255,031 (incorporated herein by reference).

Examples of clays that can be employed in the process of the present invention include kaolin, other aluminosilicate clays, Dover clay, bentonite clay, etc.

The binder employed in the present invention can include an alkali metal silicate such as an aqueous sodium silicate solution, for example, an aqueous sodium silicate solution having a total solids content of from about 38 percent by weight to about 42 percent by weight, and having a ratio of $Na_2O$ to $SiO_2$ of from about 1:2 to about 1:3.25.

In the initial step of the process of the present invention, first intermediate particles are formed by coating the inert base particles with a mixture to form a first layer on those inert base particles. Preferably, the first layer has a thickness of from about 10 µm to about 50 µm, more preferably about 30 µm. The first intermediate particles can be fired as described above to cure the binder, and to release the gaseous material from the at least one void-forming material to form the desired voids or pores in the first coating. When the void-forming material is an organic compound, the applied heat can pyrolyse the compound resulting in the desired pores. The algaecidal properties of the algae-resistant granules can be tailored by controlling the porosity and distribution of the algaecidal material. Preferably, the granules have a pore size in the range of about 0.1 µm to 20 µm.

The present process preferably further comprises forming second intermediate particles by coating the first intermediate particles with a second mixture including a coloring material to form a second layer. The second mixture can include a binder, such as a binder having the same composition as the first mixture. The second intermediate particles are fired to cure the binder. The second mixture can optionally include a void-forming material, so as to increase the porosity of the cured coating ultimately formed. Further, the second mixture can optionally include at least one algaecidal material, such as cuprous oxide. Preferably, the second layer has a thickness of from about 2 µm to about 25 µm, more preferably about 5 µm. Preferably, the second intermediate particles are formed by coating the first intermediate particles without firing the first intermediate particles to cure the first binder. This reduces the energy required to produce the algae-resistant particles of the present invention by reducing the number of energy-consuming firing steps from two to one.

In alternative embodiment of the process of the present invention, the inert base particles are coated with a single mixture including binder, at least one void-forming material, at least one algaecidal material, and at least one colorant, to provide "intermediate" particles. The intermediate particles are subsequently fired at elevated temperature to both cure the binder and decompose the at least one void-forming material thus providing the desired voids or pores in the granule coating.

The algae-resistant roofing granules of the present invention can be colored using conventional coatings pigments. Examples of coatings pigments that can be used include those provided by the Color Division of Ferro Corporation, 4150 East 56th St., Cleveland, Ohio 44101, and produced using high temperature calcinations, including PC-9415 Yellow, PC-9416 Yellow, PC-9158 Autumn Gold, PC-9189 Bright Golden Yellow, v-9186 Iron-Free Chestnut Brown, V-780 Black, V0797 IR Black, V-9248 Blue, PC-9250 Bright Blue, PC-5686 Turquoise, V-13810 Red, V-12600 Camouflage Green, V12560 IR Green, V-778 IR Black, and V-799 Black. Further examples of coatings pigments that can be used include white titanium dioxide pigments provided by Du Pont de Nemours, P.O. Box 8070, Wilmington, Del. 19880.

The algaecide resistance properties of the algaecide resistant roofing granules of the present invention are determined by a number of factors, including the porosity of the roofing granules, the nature and amount(s) of the algaecide employed, and the spatial distribution of the algaecide within the granules.

The process of the present invention advantageously permits the algae resistance of the shingles employing the algae-resistant granules to be tailored to specific local conditions. For example, in geographic areas encumbered with excessive moisture favoring rapid algae growth, the granules can be structured to release the relatively high levels of algaecide required to effectively inhibit algae growth under these conditions. Conversely, where algae growth is less favored by local conditions, the granules can be structured to release the lower levels of algaecide effective under these conditions.

The algae resistance properties of the granule bodies can also be varied through control of the porosity conferred by the binder employed. For example, the binder porosity can be controlled by adjusting the ratio of the aqueous silicate and the aluminosilicate employed.

Combinations of the above-described alternatives for introducing algaecide into and/or on the granule bodies can also be employed. By adjusting the amount and selecting the type of algaecide used, and by adjusting the porosity of the granules, a variety of different algaecide leach rates and leaching profiles can be obtained.

The algae-resistant granules prepared according to the process of the present invention can be employed in the manufacture of algae-resistant roofing products, such as algae-resistant asphalt shingles, using conventional roofing production processes. Typically, bituminous roofing products are sheet goods that include a non-woven base or scrim formed of a fibrous material, such as a glass fiber scrim. The base is coated with one or more layers of a bituminous material such as asphalt to provide water and weather resistance to the roofing product. One side of the roofing product is typically coated with mineral granules to provide durability, reflect heat and solar radiation, and to protect the bituminous binder from environmental degradation. The algae-resistant granules of the present invention can be mixed with conventional roofing granules, and the granule mixture can be embedded in the surface of such bituminous roofing products using conventional methods. Alternatively, the algae-resistant granules of the present invention can be substituted for conventional roofing granules in manufacture of bituminous roofing products to provide those roofing products with algae-resistance.

Bituminous roofing products are typically manufactured in continuous processes in which a continuous substrate sheet of a fibrous material such as a continuous felt sheet or glass fiber mat is immersed in a bath of hot, fluid bituminous coating material so that the bituminous material saturates the substrate sheet and coats at least one side of the substrate. The reverse side of the substrate sheet can be coated with an anti-stick material such as a suitable mineral powder or a fine sand. Roofing granules are then distributed over selected portions of the top of the sheet, and the bituminous material serves as an adhesive to bind the roofing granules to the sheet when the bituminous material has cooled. The sheet can then be cut into conventional shingle sizes and shapes (such as one foot by three feet rectangles), slots can be cut in the shingles to provide a plurality of "tabs" for ease of installation, additional bituminous adhesive can be applied in strategic locations and covered with release paper to provide for securing successive courses of shingles during roof installation, and the finished shingles can be packaged. More complex methods of shingle construction can also be employed, such as building up multiple layers of sheet in selected portions of the shingle to provide an enhanced visual appearance, or to simulate other types of roofing products.

The bituminous material used in manufacturing roofing products according to the present invention is derived from a petroleum-processing by-product such as pitch, "straight-run" bitumen, or "blown" bitumen. The bituminous material can be modified with extender materials such as oils, petroleum extracts, and/or petroleum residues. The bituminous material can include various modifying ingredients such as polymeric materials, such as SBS (styrene-butadiene-styrene) block copolymers, resins, flame-retardant materials, oils, stabilizing materials, anti-static compounds, and the like. Preferably, the total amount by weight of such modifying ingredients is not more than about 15 percent of the total weight of the bituminous material. The bituminous material can also include amorphous polyolefins, up to about 25 percent by weight. Examples of suitable amorphous polyolefins include atactic polypropylene, ethylene-propylene rubber, etc. Preferably, the amorphous polyolefins employed have a softening point of from about 130 degrees C. to about 160 degrees C. The bituminous composition can also include a suitable filler, such as calcium carbonate, talc, carbon black, stone dust, or fly ash, preferably in an amount from about 10 percent to 70 percent by weight of the bituminous composite material.

The following examples are provided to better disclose and teach processes and compositions of the present invention. They are for illustrative purposes only, and it must be acknowledged that minor variations and changes can be made without materially affecting the spirit and scope of the invention as recited in the claims that follow.

EXAMPLE 1

1,000 g of crushed and screened rhyolite igneous rock from Wrentham, Mass. having an average particle size of 1 mm are mixed for 2 minutes in a paddle mixer with 40 g of aqueous sodium silicate (40% solids, with $Na_2O:SiO_2$ ratio of 1:3.2) (Occidental Chemical Corporation, Dallas, Tex.), 30 g of Wilkinson brand kaolin clay, 35 g of Chemet brand cuprous oxide (American Chemet Corporation, Deerfield, Ill.) and 1.75 g of Kadox brand zinc oxide (Zinc Corporation of America, Monaca, Pa.), and 6.5 g of Regal carbon balls supplied by Cabot Corporation (Boston, Mass.) and having a chemical composition of 90% carbon black and an average particle size of 25 nm, to form green granules having a particle size of about 1 mm. The green granules are then fired in a gas-fired kiln at a temperature of 500 degrees C. for 20 minutes to form algae-resistant granules according to the present invention.

EXAMPLE 2

The process of Example 1 is repeated, except that 30 g of table sugar (Domino) having an average particle size of 20 μm is substituted for the carbon balls.

EXAMPLE 3

The process of Example 1 is repeated, except that 12 g of candy sugar "sprinkles" (Signature) having an average particle size of 1.2 mm are substituted for the carbon balls.

EXAMPLE 4

The process of Example 1 is repeated, except that 30 g of crushed walnut shells (Composite Materials, Inc.) and having an average particle size of 300 μm are substituted for the carbon balls.

EXAMPLE 5

The process of Example 3 is repeated, except that 30 g of candy sugar "sprinkles" are employed.

EXAMPLE 6

The process of Example 4 is repeated. 500 g of the granules produced are mixed with a coating mixture for 2 minutes in a paddle mixer, the coating mixture comprising 16 g of aqueous sodium silicate (40% solids, with $Na_2O:SiO_2$ ratio of 1:3.2), 10 g of kaolin clay, 6 g of V-780 (black) pigment particles (Ferro Corporation) to form coated granules (second intermediate particles) having a particle size of about 1 mm. The coated granules are then fired in a gas-fired kiln at a temperature of about 500 degrees C. for 20 minutes to form colored, algae-resistant granules according to the present invention.

EXAMPLE 7

The process of Example 6 is repeated, except that 3 g of Regal carbon balls are added to the coating mixture to increase the porosity of the fired coating.

EXAMPLE 8

The process of Example 6 is repeated, except that 7 g of Chemet brand cuprous oxide and 0.35 g of Kadox brand zinc oxide are added to the coating mixture.

EXAMPLE 9

The process of Example 6 is repeated, except that twice as much of the Chemet brand cuprous oxide was used in the inner coating, that is, 60 g of cuprous oxide for the inner coating, and 10 g of cuprous oxide is added to the outer coating, so that there is cuprous oxide in both the inner and the outer coatings.

EXAMPLE 10

The process of Example 4 is repeated, except that 70 g of Chemet brand cuprous oxide, plus 12 g of V-780 Ferro brand black pigment particles are used to form single-coated, algae-resistant granules.

COMPARATIVE EXAMPLE 1

The process of Example 1 is repeated, except that the carbon balls are omitted.

Figure 2:
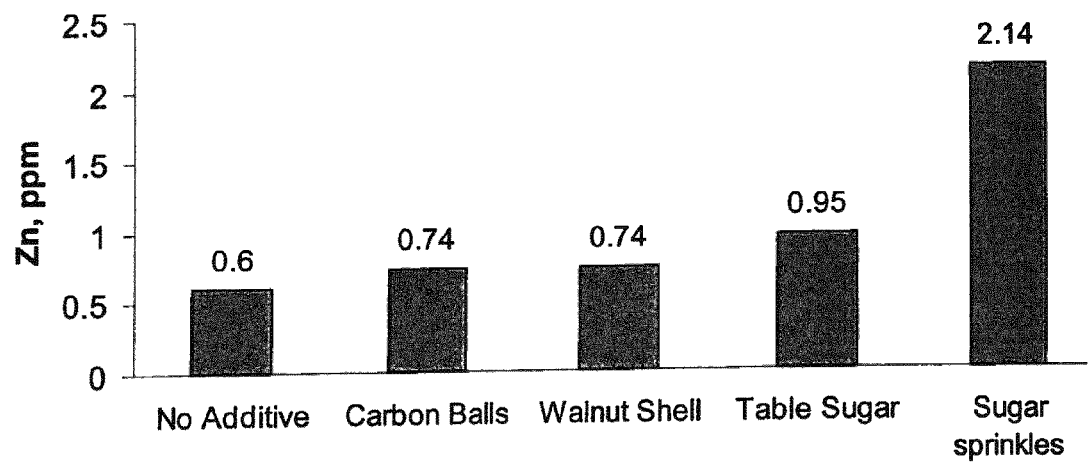
FIG. 2 is a graph illustrating the effect of various types of void-forming material on the concentrations of zinc ions leached out from granules prepared according to the present invention (after 8 days immersion in warm water of 60° C.). The values above the bars depict the copper concentrations in ppm.

The effect of varying the type of void-forming material on the algae-resistance of the algae-resistant granules of the present invention was determined. 100 g of algae-resistant granules prepared as described above in Examples 1-4 and Comparative Example 1 were immersed for 8 days in 100 g of distilled water at 60 degrees C. The concentration of copper ion and zinc ion in the leach water was then determined by inductively coupled plasma (ICP) emission spectroscopy, and the results are shown in FIGS. 1 and 2. As depicted in FIGS. 1 and 2, candy sprinkles result in much higher leaching of copper (22.24 ppm) and zinc (2.14 ppm) ions than other additives do.

Figure 3:
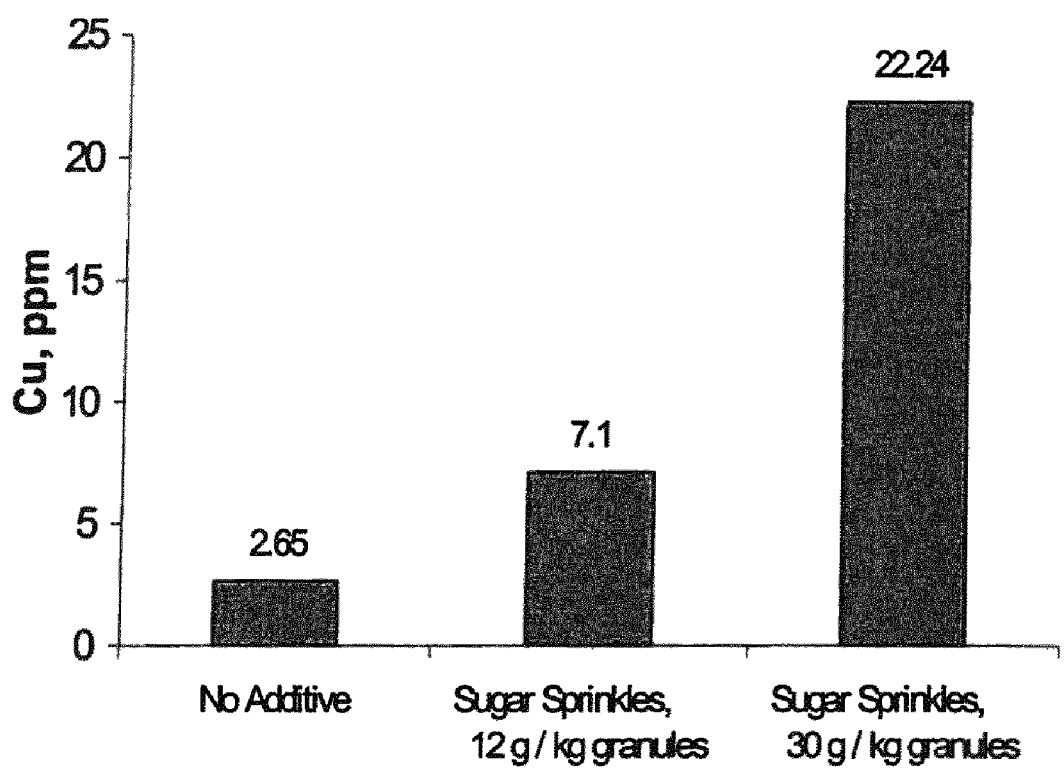
FIG. 3 is a graph illustrating the effect of varying the amount of void-forming material on the concentrations of zinc ions leached out from granules prepared according to the present invention (after 8 days immersion in warm water of 60° C.). The values above the bars depict the copper concentrations in ppm.

The effect of varying the amount of void-forming material on the algae-resistance of the algae-resistant granules of the present invention was also determined. 100 g of algae-resistant granules prepared as described in Examples 3 and 5 and Comparative Example 1 above were immersed for 8 days in 100 g of distilled water at 60 degrees C. The concentration of copper ion and zinc ion in the leach water was then determined by ICP emission spectroscopy, and the results are shown in FIG. 3. The results displayed in FIG. 3 show that granules containing a higher level of sugar sprinkles (30 g per kg of granules) leach out more copper ions than the lower sugar sprinkles or no additive.

Figure 4:
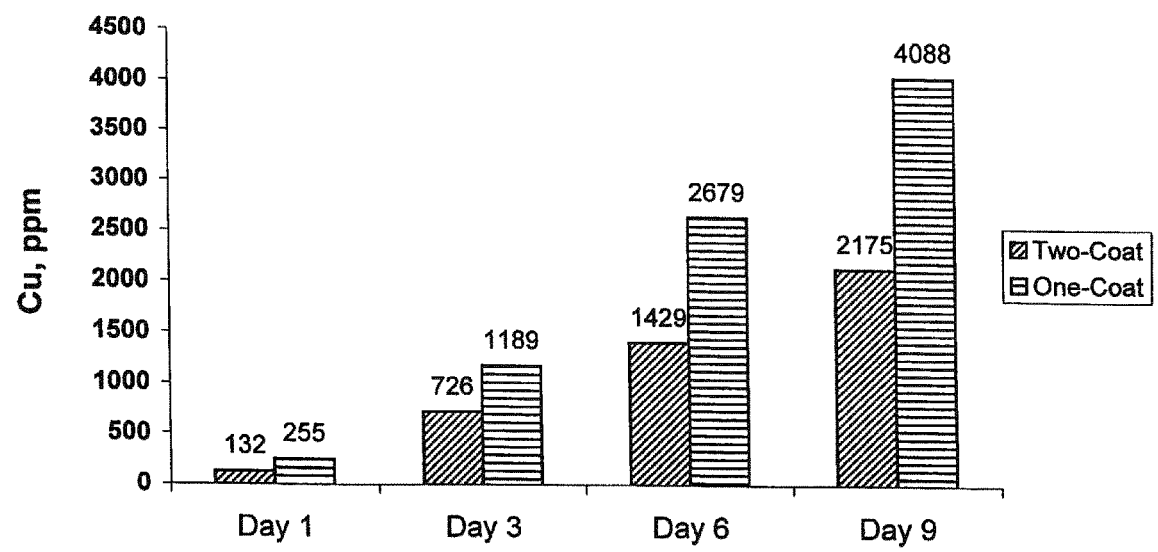
FIG. 4 is a graph comparing the leaching of copper ions from granules prepared according to the present invention coated with a single coat of a cuprous oxide coating with granules prepared with a double coat of a cuprous oxide coating.

A comparison of the leaching rates for one-coat and two-granules was made as follows:

10 g of algae-resistant granules prepared as described in Examples 9 and 10 were immersed in 10 ml of acetate buffer solution (pH 4.6) at 60° C. for various days. The concentration of cooper ions in the leached solution was determined by first reacting the copper ions with dipotassium 2,2' bicinchoninate to form a colored complex, followed by measuring the color intensity of the formed complex at 560 nm using a laboratory spectrophotometer. The results, plotted in FIG. 4, show that granules prepared by the one-coated process have higher total leached amounts of copper ions than the two-coated granules have.

Various modifications can be made in the details of the various embodiments of the processes, compositions and articles of the present invention, all within the scope and spirit of the invention and defined by the appended claims.

We claim:

1. A process for producing algae-resistant roofing shingles, the process comprising producing algae-resistant roofing granules, and adhering the granules to a shingle stock material, the algae-resistant roofing granules being produced by a process comprising:
    (a) providing inert base particles;
    (b) forming first intermediate particles by coating the inert base particles with a first mixture including;
        at least one algaecidal material, and
        a void-forming material, the void-forming material releasing gaseous material at temperatures above 90 degrees C., and having an average particle size no larger than 2 mm,
    to form a first layer on the inert base particles;
    c) forming second intermediate particles by coating the first intermediate particles with a second mixture including a coloring material and not including a void-forming material; and
    (d) heating the second intermediate particles to decompose the void-forming material and form pores in the first layer to produce the roofing granules.

2. A process according to claim 1 wherein the first mixture further includes a binder, the binder comprising an aluminosilicate material and an alkali metal silicate.

3. A process according to claim 1 wherein the second mixture further includes a binder, the binder comprising an aluminosilicate material and an alkali metal silicate.

4. A process according to claim 1 wherein the at least one algaecidal material is selected from the group consisting of copper compounds and zinc compounds.

5. A process according to claim 4 wherein the at least one algaecidal material comprises cuprous oxide.

6. A process according to claim 5 wherein the cuprous oxide comprises at least 2 percent of the algae resistant granules.

7. A process according to claim 5 wherein the at least one algaecidal material further comprises zinc oxide.

8. A process according to claim 7 wherein the zinc oxide comprise at least 0.1 percent by weight of the algae-resistant granules.

9. A process according to claim 1 wherein the void-forming material comprises a substance selected from the group comprising ground walnut shells, sugar, and carbon black.

10. A process according to claim 8 wherein the void-forming material comprises at least 0.1 percent by weight of the algae-resistant granules.

11. A process according to claim 1 wherein the coloring material is selected from the group comprising transition metal oxides.

12. A process according to claim 1 wherein the second intermediate particles are heated to a temperature of at least 500 degrees C.

13. A process according to claim 1 wherein the granules have a pore size in the range of about 0.1 to 20 micrometers.

14. A process according to claim 1 wherein the first intermediate layer has a thickness of about 30 micrometers.

15. A process according to claim 1 wherein the second intermediate layer has a thickness of about 5 micrometers.

16. A process according to claim 1 wherein the second mixture further includes at least one algaecidal material.

17. A process for producing algae-resistant roofing shingles, the process comprising producing algae-resistant roofing granules, and adhering the granules to a shingle stock material, the algae-resistant roofing granules being produced by a process comprising:
   (a) providing inert base particles;
   (b) forming first intermediate particles by coating the inert base particles with a first mixture including;
      a binder;
      at least one algaecidal material, and
      a void-forming material, the void-forming material releasing gaseous material at temperatures above 90 degrees C., and having an average particle size no larger than 2 mm, to form a first layer on the inert base particles;
   (c) forming second intermediate particles by coating the first intermediate particles with a second mixture including a binder and a coloring material and not including a void-forming material to form a second coating having a thickness of from about 2 micrometers to about 25 micrometers; and
   (d) heating the second intermediate particles to release the gaseous material and form pores in the first layer to produce the roofing granules.

18. A process according to claim 17 wherein the at least one algaecidal material is selected from the group consisting of copper compounds and zinc compounds.

19. A process according to claim 18 wherein the at least one algaecidal material is cuprous oxide; the cuprous oxide comprising at least 2 percent of the algae resistant granules.

* * * * *

UNITED STATES PATENT AND TRADEMARK OFFICE
CERTIFICATE OF CORRECTION

| | | |
|---|---|---|
| PATENT NO. | : 8,039,048 B2 | Page 1 of 1 |
| APPLICATION NO. | : 12/610782 | |
| DATED | : October 18, 2011 | |
| INVENTOR(S) | : Keith C. Hong, Husnu M. Kalkanoglu and Ming Liang Shiao | |

It is certified that error appears in the above-identified patent and that said Letters Patent is hereby corrected as shown below:

Page 2, line 9, OTHER PUBLICATIONS, Minerals Research & Recovery, Inc. "Roofing Granules," 2 pgs.
        reads "(Tuscan, AZ) date unknown."
    should read -- (Tucson, AZ) date unknown." --

Column 4, line 26, reads "from about 0.2 mm to about 3 mm, and more preferable from"
        should read -- from about 0.2 mm to about 3 mm, and more preferably from --

Column 5, line 50, reads "250 degree C. to 400 degrees C, such as disclosed in U.S. Pat."
        should read -- 250 degrees C. to 400 degrees C, such as disclosed in U.S. Pat. --

Column 6, line 27, reads "In alternative embodiment of the process of the present"
        should read -- In an alternative embodiment of the process of the present --

Column 6, line 43, reads "Golden Yellow, v-9186 Iron-Free Chestnut Brown, V-780"
        should read -- Golden Yellow, V-9186 Iron-Free Chestnut Brown, V-780 --

Column 6, line 44, reads "Black, V0797 IR Black, V-9248 Blue, PC-9250 Bright Blue,"
        should read -- Black, V-0797 IR Black, V-9248 Blue, PC-9250 Bright Blue, --

Column 8, line 23, reads "sodium silicate (40% solids, with $Na_2O;SiO_2$ ration of 1:3.2)"
        should read -- sodium silicate (40% solids, with $Na_2O;SiO_2$ ratio of 1:3.2) --

Column 9, line 67, reads "tion of cooper ions in the leached solution was determined by"
        should read -- tion of copper ions in the leached solution was determined by --

Column 10, line 52, reads "comprise at least 0.1 percent by weight of the algae-resistant"
        should read -- comprises at least 0.1 percent by weight of the algae-resistant --

Signed and Sealed this
Thirteenth Day of December, 2011

David J. Kappos
*Director of the United States Patent and Trademark Office*